United States Patent
Nakaishi et al.

(10) Patent No.: US 11,273,474 B2
(45) Date of Patent: Mar. 15, 2022

(54) ION GENERATING DEVICE FOR ORGANIC MATTER DECOMPOSITION, AND ORGANIC MATTER DECOMPOSITION DEVICE

(71) Applicant: GLENCAL TECHNOLOGY CO., LTD., Tokyo (JP)

(72) Inventors: Masahito Nakaishi, Tokyo (JP); Koji Irie, Osaka (JP)

(73) Assignee: GLENCAL TECHNOLOGY CO., LTD., Tokyo (JP)

( * ) Notice: Subject to any disclaimer, the term of this patent is extended or adjusted under 35 U.S.C. 154(b) by 0 days.

(21) Appl. No.: 16/965,598

(22) PCT Filed: Jan. 29, 2019

(86) PCT No.: PCT/JP2019/002989
§ 371 (c)(1),
(2) Date: Jul. 28, 2020

(87) PCT Pub. No.: WO2019/146799
PCT Pub. Date: Aug. 1, 2019

(65) Prior Publication Data
US 2021/0039145 A1 Feb. 11, 2021

(30) Foreign Application Priority Data
Jan. 29, 2018 (JP) .............................. JP2018-012755

(51) Int. Cl.
*B09B 3/00* (2022.01)
*H01T 19/04* (2006.01)
(Continued)

(52) U.S. Cl.
CPC .................. *B09B 3/00* (2013.01); *A61L 2/02* (2013.01); *A61L 9/22* (2013.01); *H01T 19/04* (2013.01);
(Continued)

(58) Field of Classification Search
None
See application file for complete search history.

(56) References Cited

U.S. PATENT DOCUMENTS 5,549,795 A * 8/1996 Gregoire ................. H01T 19/00
204/164
5,649,507 A * 7/1997 Gregoire ............... C02F 1/4608
123/143 B
(Continued)

FOREIGN PATENT DOCUMENTS

JP 2004-66196 3/2004
JP 2004-167318 6/2004
(Continued)

OTHER PUBLICATIONS

International Search Report dated Jun. 18, 2019 in International Application No. PCT/JP2019/002989.

*Primary Examiner* — Kevin R Steckbauer
(74) *Attorney, Agent, or Firm* — Wentsler LLC

(57) ABSTRACT

Provided is an ion generating device for organic matter decomposition for generating ions to decompose organic matter stored in a tank. The ion generating device includes a needle electrode and a plate electrode, both facing each other, and a direct-current power supply unit configured to apply a direct-current voltage with positive polarity to the needle electrode. The direct-current power supply unit includes a voltage controller configured to set the direct-current voltage to a specified voltage value to produce positive corona discharge between the needle electrode and the plate electrode under atmospheric pressure.

6 Claims, 7 Drawing Sheets

(51) Int. Cl.
  *A61L 2/02* (2006.01)
  *A61L 9/22* (2006.01)
  *H01T 19/00* (2006.01)
  *H01T 19/02* (2006.01)
  *A61L 11/00* (2006.01)

(52) U.S. Cl.
  CPC ............... *A61L 11/00* (2013.01); *H01T 19/00* (2013.01); *H01T 19/02* (2013.01)

(56) References Cited

U.S. PATENT DOCUMENTS

| | | | | |
|---|---|---|---|---|
| 5,655,210 | A * | 8/1997 | Gregoire | C02F 1/4608 422/186 |
| 9,468,937 | B2 * | 10/2016 | Tanaka | A61L 9/22 |
| 10,581,227 | B2 * | 3/2020 | Haruna | A61L 9/22 |
| 2003/0108460 | A1 * | 6/2003 | Andreev | B01D 53/32 422/186.07 |
| 2004/0028572 | A1 * | 2/2004 | Sham | A61L 2/202 422/123 |
| 2014/0326809 | A1 * | 11/2014 | Muller | B09B 3/00 241/1 |
| 2015/0224516 | A1 * | 8/2015 | Tanaka | A61L 9/22 96/24 |
| 2017/0232127 | A1 * | 8/2017 | Bakanas | A61L 2/24 422/105 |
| 2017/0346261 | A1 * | 11/2017 | Haruna | H01T 23/00 |
| 2019/0210038 | A1 * | 7/2019 | Kuroi | A61L 9/22 |
| 2020/0238350 | A1 * | 7/2020 | Zhang | B65F 3/001 |
| 2020/0392669 | A1 * | 12/2020 | Imai | G01N 33/34 |

FOREIGN PATENT DOCUMENTS

| | | | | |
|---|---|---|---|---|
| JP | 2007-864 | | 1/2007 | |
| JP | 2011-230082 | | 11/2011 | |
| JP | 2016-9674 | | 1/2016 | |
| JP | 2016009674 | A * | 1/2016 | ............ H01T 19/04 |
| JP | 2017-189413 | | 10/2017 | |

* cited by examiner

ION GENERATING DEVICE FOR ORGANIC MATTER DECOMPOSITION, AND ORGANIC MATTER DECOMPOSITION DEVICE

TECHNICAL FIELD

The present invention relates to an ion generating device for organic matter decomposition, and to an organic matter decomposition device. The present invention is suitable for use in an organic matter decomposition device for decomposing food waste such as vegetable waste.

BACKGROUND ART

Conventional food waste disposers have been known to use active oxygen species in order to decompose organic matter such as food waste (See Patent Literature 1, for example). Patent Literature 1 discloses a decomposition of food waste in a tank using, as active oxygen species, superoxide ($O_2.-$), hydroxyl radical (.OH), hydrogen peroxide ($H_2O_2$), singlet oxygen ($^1O_2$), ozone ($O_3$), and so on.

Such food waste disposers using active oxygen species have advantages over food waste disposers using bacterium in terms of inhibiting production of methane gas during the decomposition and preventing foul smell.

CITATION LIST

Patent Literature

Patent Literature 1: Japanese Laid-Open Patent Publication No. 2017-189413

SUMMARY OF INVENTION

Technical Problem

In such a food waste disposer, various kinds of organic matter other than food waste, such as paper material, may be mixed in with the food waste. In light of extra work for waste sorting, it is desirable to develop an organic matter decomposition device having higher decomposition capability than ever before. Also from a viewpoint of further reduction in amount of time needed for decomposition, it is desirable to enhance the decomposition capability.

In view of the foregoing, an object of the present invention is to provide an ion generating device for organic matter decomposition, and an organic matter decomposition device that are able to enhance decomposition capability of organic matter more than ever before.

Solution to Problem

An ion generating device for organic matter decomposition according to the invention is an ion generating device for organic matter decomposition for generating ions to decompose organic matter stored in a tank. The ion generating device includes a needle electrode and a plate electrode, both facing each other, and a direct-current power supply unit configured to apply a direct-current voltage with positive polarity to the needle electrode. The direct-current power supply unit includes a voltage controller configured to set the direct-current voltage to a specified voltage value to produce positive corona discharge between the needle electrode and the plate electrode under atmospheric pressure.

An organic matter decomposition device according to the invention includes the ion generating device for organic matter decomposition described above, and the tank on which the ion generating device for organic matter decomposition is provided.

Advantageous Effects of Invention

According to the present invention, it is possible to generate oxonium ions having high decomposition capability of organic matter. Hence, the use of the oxonium ions leads to enhancement of decomposition capability of organic matter more than ever before.

DESCRIPTION OF EMBODIMENT

Embodiments of the present invention will be described below with reference to the drawings.

<Configuration of Organic Matter Decomposition Device of Present Invention>

Figure 1:
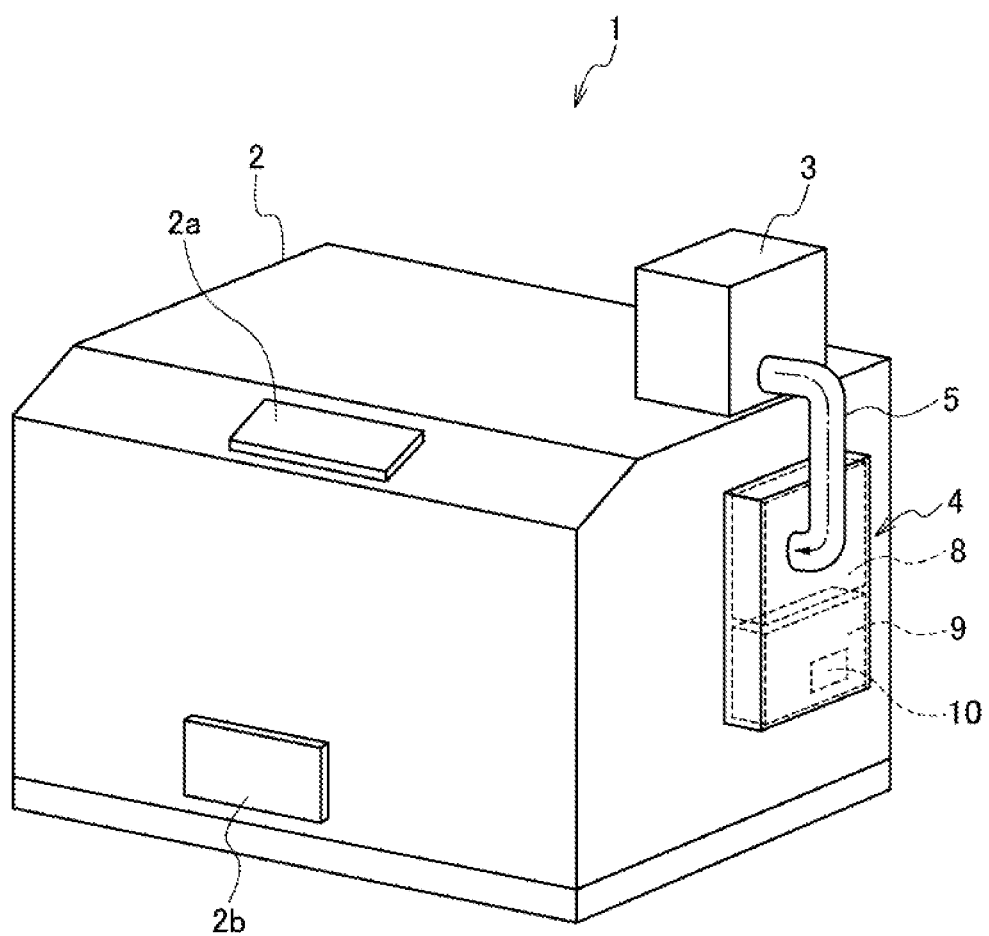
FIG. 1 is a schematic view of an entire configuration of an organic matter decomposition device according to the present invention.

FIG. 1 is a schematic view of an entire configuration of an organic matter decomposition device 1 according to the present invention. The organic matter decomposition device 1 is configured to decompose food waste such as vegetable waste and other various kinds of organic matter such as polymer and paper material, using oxonium ions. Oxonium ions are positive ions, and examples of oxonium ions include hydronium ions, oxatriquinane, and oxatriquinacene. In this embodiment, the organic matter decomposition device 1 includes a tank 2 into which organic matter is configured to be introduced, a blower 3, and an ion generating device 4 for organic matter decomposition.

Organic matter to be decomposed is introduced into the tank 2 through an inlet opening 2a, and stored inside the tank 2. The decomposed organic matter can be discharged from the tank 2 through an outlet opening 2b into the outside environment. In this embodiment, the organic matter decomposition device 1 includes therein a heater and a stirring device, both of which are not shown in the drawings, for heating and stirring organic matter in the tank 2 while irradiating the organic matter with oxonium ions generated by the ion generating device 4 for organic matter decomposition to dehydrate and decompose the organic matter.

The blower 3 and the ion generating device 4 for organic matter decomposition are placed at predetermined locations on the tank 2, and connected to each other via a pipe 5. The blower 3 sucks air into the ion generating device 4 for organic matter decomposition via the pipe 5. The gas, which has been sucked into the ion generating device 4 for organic matter decomposition by the blower 3, passes through the ion generating device 4 for organic matter decomposition and flows into the tank 2.

The ion generating device 4 for organic matter decomposition includes a housing 8 within which an electrode structure, which will be described later, is placed, and includes a direct-current power supply unit 9. The housing 8 includes an inlet (not shown in the drawings) which is connected to the pipe 5 and through which the gas from the blower 3 is configured to be introduced into the housing 8. The housing 8 further includes an outlet (not shown in the drawings) which leads to the tank 2 and through which the gas from the blower 3 is configured to flow into the tank 2.

In the housing 8, a hermetically sealed space is provided, into which the gas from the blower 3 is configured to be introduced to form a gas flow from the inlet toward the outlet via the electrode structure (which will be described later). As a result, oxonium ions generated within the housing 8 flows into the tank 2 through the outlet.

The direct-current power supply unit 9 is configured to generate a direct-current voltage with positive polarity and apply the DC voltage to the electrode structure in the housing 8. The direct-current power supply unit 9 includes a voltage controller 10 configured to control a voltage value of the DC voltage. The voltage controller 10 is configured to set the DC voltage to a specified voltage value. This causes the electrode structure to produce positive corona discharge and to generate oxonium ions. In order to generate the oxonium ions having high decomposition capability of organic matter, the voltage controller 10 is configured to set the DC voltage to an optimal voltage value.

<Regarding Electrode Structure>

Figure 2A:
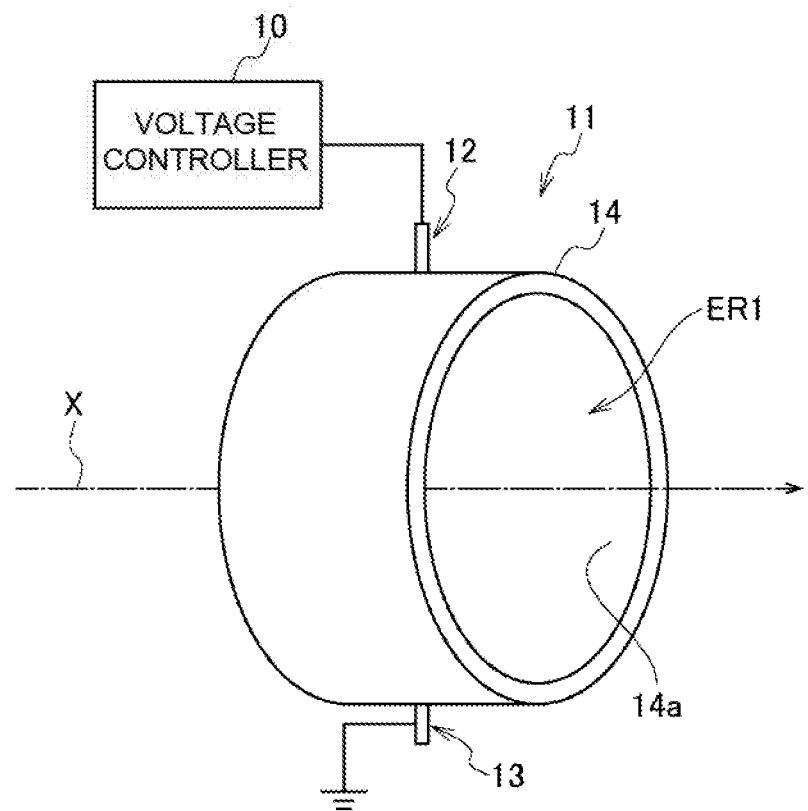
FIG. 2A is a schematic view of a configuration of an electrode structure.

Next, reference will be made below to the electrode structure placed within the housing 8 of the ion generating device 4 for organic matter decomposition. As shown in FIG. 2A, the electrode structure 11 includes a needle electrode 12, a plate electrode 13 and an electrode supporting member 14. The electrode supporting member 14 is made of insulating material such as polyvinyl chloride, and has a cylindrical tube shape to support the needle electrode 12 and the plate electrode 13.

Although the cylindrical tube-shaped electrode supporting member 14 is employed as a tubular electrode supporting member in this embodiment, the present invention is not limited to such a shape of the electrode supporting member. The electrode supporting member may have a polygonal tubular shape such as a quadrangular tubular shape.

The electrode supporting member 14 supports the needle electrode 12 and the plate electrode 13 such that the needle electrode 12 and the plate electrode 13 face each other in a hollow space ER1 surrounded by a tubular inner wall 14a. The electrode supporting member 14 is placed between the inlet and outlet (not shown in the drawings) of the housing 8 (FIG. 1). With this structure, the introduction of the gas from the blower 3 into the housing 8 through the inlet causes the gas flow in the hollow space ER1 in one direction (e.g., in an arrow direction of a central axis X) along the central axis X within the hollow space ER1.

More specifically, it is desirable that the electrode supporting member 14 should be placed within the housing 8 such that the inlet and outlet of the housing 8 are located on the central axis X of the hollow space ER1. In particular, an opening end in the hollow space ER1 of the electrode supporting member 14 is oriented to the outlet of the housing 8 to form the gas flow connecting between the hollow space ER1 and the outlet with a straight line. This can prevent oxonium ions (which will be described later) generated within the hollow space ER1 from hitting against the inner wall and other elements of the housing 8, thereby leading the oxonium ions directly to the outlet.

Figure 2B:
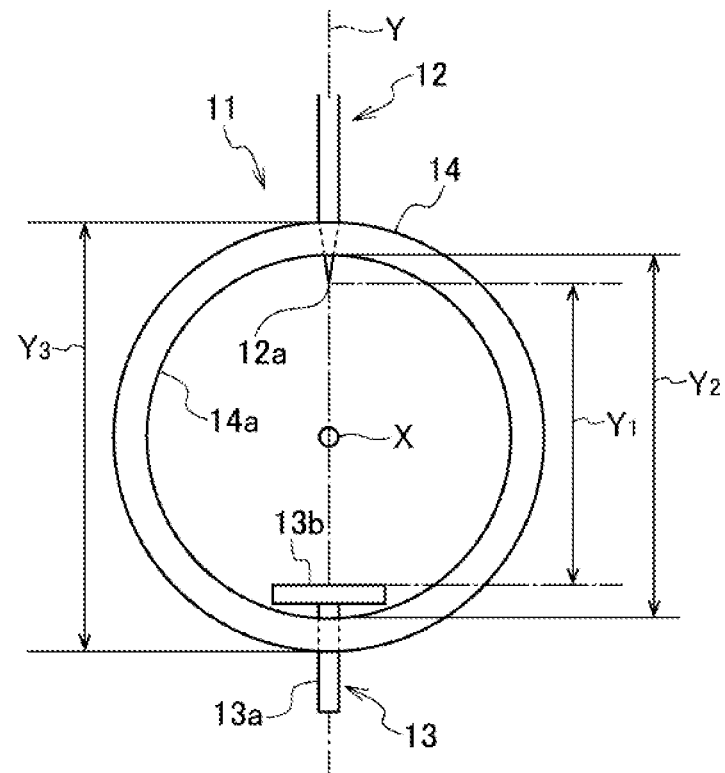
FIG. 2B is a schematic front elevational view of the electrode structure.

As shown in FIG. 2B, the electrode supporting member 14 has an inner diameter $Y_2$ of 25±5 mm of the tubular inner wall 14a, and has an outer diameter $Y_3$ of 32±5 mm, for example.

As shown in FIG. 2B, the needle electrode 12 and the plate electrode 13 are placed on an orthogonal line Y to the central axis X so as to face each other. The plate electrode 13 includes a flat plate portion 13b that is located immediately below a needle-shaped tip portion 12a of the needle electrode 12. The needle electrode 12 is made of metal material such as tungsten, and has a diameter of 0.1 mm to 2.0 mm. The needle electrode 12 penetrates through the tubular inner wall 14a of the electrode supporting member 14 to expose the needle-shaped tip portion 12a in the hollow space ER1.

The plate electrode 13 is made of metal material such as stainless steel, and includes a rod-shaped support portion 13a and the flat plate portion 13b provided on an end of the support portion 13a. The flat plate portion 13b has a disk shape with a diameter of 5 mm to 20 mm and a thickness of 1.5±1.0 mm. The support portion 13a penetrates through the tubular inner wall 14a of the electrode supporting member 14 to expose the flat plate portion 13b in the hollow space ER1.

Although the needle electrode 12 and the support portion 13a of the plate electrode 13 penetrate through the tubular inner wall 14a in this embodiment, the present invention is not limited to such a structure. For example, a base end of the needle electrode 12 may be fixed to a surface of the tubular inner wall 14a so that the needle electrode 12 does not penetrate through the tubular inner wall 14a. The support portion 13a or the flat plate portion 13b may also be fixed to the surface of the tubular inner wall 14a so that the plate electrode 13 does not penetrate through the tubular inner wall 14a, either.

An interelectrode distance $Y_1$ between the needle-shaped tip portion 12a of the needle electrode 12 and the flat plate portion 13b of the plate electrode 13 facing the needle-shaped tip portion 12a is designed to be 20 mm, for example. The interelectrode distance $Y_1$ is not limited to 20 mm, but is defined based on the voltage value (kV) of the DC voltage with positive polarity, which will be described later, and on an electrical field strength (kV/mm).

Here, as shown in FIG. 2A, the base of the needle electrode 12 is exposed on the outside of the electrode supporting member 14, and is connected to the voltage controller 10. In this embodiment, the plate electrode 13 is grounded. Instead of being grounded, the plate electrode 13 may be connected to the voltage controller 10 to apply a DC voltage with negative polarity, serving as a negative electrode.

If the plate electrode 13 is grounded, it is desirable that the voltage controller 10 apply, to the needle electrode 12, the DC voltage with positive polarity, having the electrical field strength of 0.25 kV/mm to 1.50 kV/mm and the voltage value of 5 kV to 30 kV. If the DC voltage with positive polarity has the electrical field strength of 0.25 kV/mm to 1.50 kV/mm, it is possible to stably produce positive corona discharge at the interelectrode distance $Y_1$.

If the voltage value of the DC voltage with positive polarity is less than 5 kV, it is difficult to generate sufficient oxonium ions for decomposition of organic matter even if the electrical field strength of the DC voltage is within a range of 0.25 kV/mm to 1.50 kV/mm. If the voltage value of the DC voltage with positive polarity is greater than 30 kV, conditions for maintaining the stability of discharge are much more severe than those when the voltage value is not greater than 30 kV, which may reduce the usefulness of the organic matter decomposition device in view of maintenance or other factors. It is therefore desirable that the electrical field strength of the DC voltage be 0.25 kV/mm to 1.50 kV/mm, and the voltage value of the DC voltage with positive polarity be 5 kV to 30 kV.

When the DC voltage having the above-described voltage value is applied to the needle electrode 12 in this way, a static non-uniform electric field is generated between the needle electrode 12 and the plate electrode 13 under atmospheric pressure, thus positive corona discharge is produced. This can lead to generating oxonium ions within the hollow space ER1 which is a discharge space.

Reference will be made to a difference between vacuum discharge and atmospheric discharge. Let us consider the situation of varying the voltage and the interelectrode distance with fixed kV/mm using the same needle electrode 12 and plate electrode 13. In a vacuum, electrical field strength distributions have a similar shape. In ambient air, on the other hand, electrical field strength distributions do not always have a similar shape due to the presence of a slight amount of positive and negative ions. The larger the interelectrode distance, the higher the influence of the positive and negative ions, making it difficult to secure the stability of discharge.

Here, one of main reactions for generating ions in the discharge space is a molecular ion-generating reaction. In order to ionize gas molecules M to produce molecular ions $M^+$ and electrons $e^-$, there is need to provide the gas molecules M with larger energy than ionization energy for the gas molecules M. This energy is caused by collision of electrons accelerated in a glow region of a high electrical field in the discharge space under the atmospheric pressure.

Primary ions generated by the discharge travel in the electric field along lines of electric force according to their polarity. The primary ions travel a mean free path toward the plate electrode 13 before colliding with by-products of discharge derived from neutral radical species A., [M-B]. and B. and another gas in the discharge space to cause various ion-molecule reactions, thereby transforming to ionic species with longer life-span. This process continuously occurs while moving a drift region, and terminal ions are generated through successive ion-molecule reactions.

In positive corona discharge in ambient air, the terminal ions are oxonium ions irrespective of discharge conditions. Formation and evolution of oxonium ions in positive corona discharge in ambient air are estimated based on a measured value of each elementary reaction rate constant. This shows, for example, that a hydronium ion, which is an example of an oxonium ion, is generated via evolution mostly involving $H_2O$, using, as primary ions, $N_2^+$. and $O_2^+$. generated by ionization in a glow region.

<Oxidation Power of Oxonium Ion>

Next, oxidation power of an oxonium ion will be described. An atom becomes stable by releasing energy. Electron affinity is defined as energy released when an electron is added to the outermost shell of the atom. A large electron affinity of an atom indicates that the atom is more likely to gain an electron from another object to become stable. That is, large electron affinity represents strong oxidation power.

Figure 3:
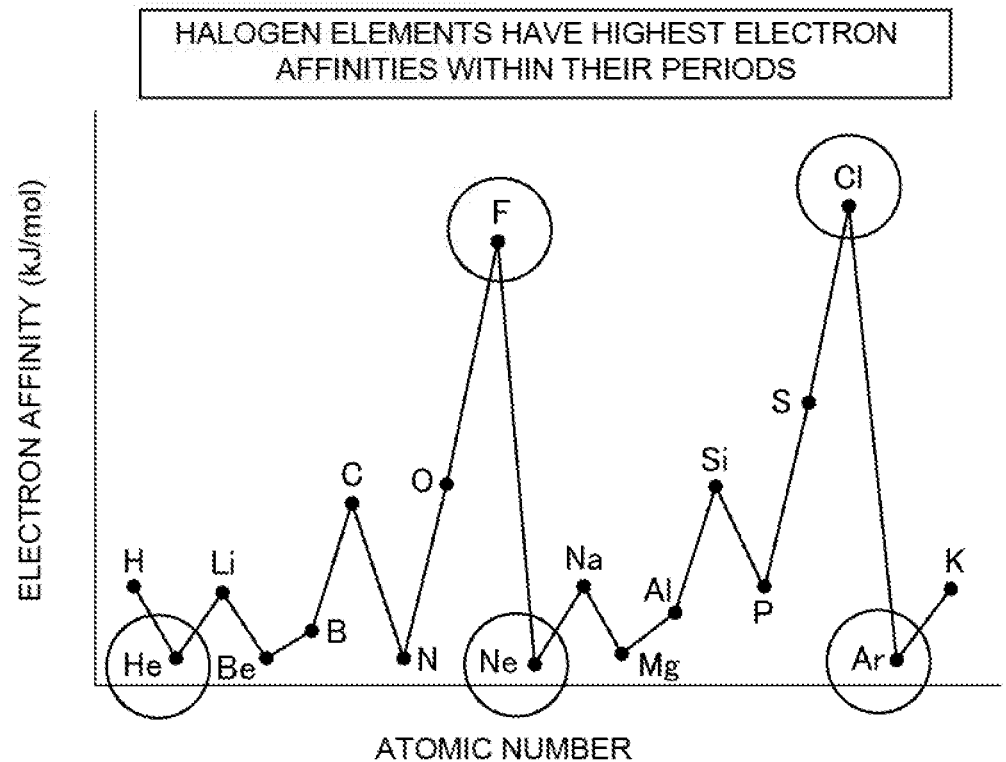
FIG. 3 is a graph illustrating electron affinity.

FIG. 3 is a graph illustrating a relationship between atomic number and electron affinity. Halogen elements such as fluorine (F) and chlorine (Cl) have highest electron affinities within their periods. The electron affinity of chlorine is 3.617 eV, which is extremely large. The ionization usually creates a monovalent anion. Here, let us consider electron affinity of a monovalent cation of an atom. The first ionization energy of an atom is defined as energy needed to remove an electron from the outermost shell of the atom to form a monovalent cation. That is, "electron affinity of a monovalent cation of an atom" is equivalent to "the first ionization energy of the atom."

Noble gases have a large amount of first ionization energy within their periods, however, it is difficult to ionize noble gases by electric discharge or other methods, for example. Nitrogen, oxygen, fluorine and chlorine are the only elements that have a higher first ionization energy than hydrogen except for noble gases. Basically, neither fluorine nor chlorine exists freely in nature. Neither nitrogen nor oxygen can be converted into a monovalent cation by electric discharge or other methods, for example. Hence, the hydrogen ion has the largest electron affinity among monovalent cations.

A hydronium ion, which is an example of an oxonium ion, is a bond between $H^+$ and $H_2O$, thus the hydronium ion is believed to share the same electron affinity (oxidation power) with the hydrogen ion, which is about 13.6 eV. This value indicates that the oxidation power of the hydronium ion is much larger than redox potential of active oxygen species.

Next, a verification test for identifying strength of the oxidation power of oxonium ions is conducted. In this verification test, the electrode structure 11 shown in FIGS. 2A and 2B is prepared and used to generate oxonium ions. The exemplary electrode structure 11 is prepared using the needle electrode 12 made of tungsten and having a diameter of 1 mm, the disk-shaped plate electrode 13 made of stainless steel and having a diameter of 10 mm and a thickness of 1.5 mm, and the electrode supporting member 14 made of polyvinyl chloride and having an inner diameter $Y_2$ of 25 mm, an outer diameter $Y_3$ of 32 mm and a thickness of 1.4 mm.

In this typical example, the interelectrode distance $Y_1$ is 20 mm, the DC voltage with positive polarity of 20 kV is applied to the needle electrode 12, and the plate electrode 13 is grounded. Under this condition, it is found that electric discharge occurs between the needle electrode 12 and the plate electrode 13. This electric discharge is positive corona discharge because the DC voltage with positive polarity is applied to the needle electrode 12, and the plate electrode 13 is grounded.

Subsequently, plural iron nails are prepared, and the opening end of the electrode supporting member 14 is moved closer to the iron nails to continuously produce the positive corona discharge for about 48 hours. Separately from this test, as a comparative example, ionizer and ozonizer (Ionizer MHM305 manufactured by Murata Manufacturing Co., Ltd., and Ionizer/Ozonizer MHM306 manufactured by Murata Manufacturing Co., Ltd.) are prepared to continuously irradiate plural iron nails with negative ions and ozone for about 48 hours in a similar way. The condition for the irradiation is to continuously irradiate the plural iron nails with negative ions and ozone for about 48 hours in a similar way. The voltage of 2 kV is applied per product specifications.

As a result, in the typical example, visual observation indicates that the iron nails are darkly discolored over the entire surfaces thereof, forming rust. In the comparative example, on the other hand, visual observation indicates that the surfaces of the iron nails remain nearly silver-colored from the beginning, rarely forming rust. As just described, it is found that the oxidation power in the typical example is stronger than that in the comparative example using active oxygen species.

<Relationship Between Oxidation Power and Drying Capacity of Oxonium Ions>

Here, water has a boiling point of 100° C. and a heat of vaporization of 2250 kJ/kg. Ethanol has a boiling point of 80.3° C. and a heat of vaporization of 393 kJ/kg. Ether has a boiling point of 34.5° C. and a heat of vaporization of 327 kJ/kg. As just described, water has a huge heat of vaporization. This may be because a water molecule is polar, which enables hydrogen bonding and formation of clusters.

The heat of vaporization of water, which is 2250 kJ/kg, is calculated to be about 0.4 eV per water molecule. For example, when hydronium ions approach clustered water molecules, the oxidation power (electron affinity) of 13.6 eV can be expected to remove an electron which forms hydrogen bonding to allow the electron to become a free electron with high energy (about 13 eV). It is expected that the high-energy free electron will collide with a different electron which also forms hydrogen bonding to allow the different electron to become another high-energy free electron.

The irradiation with oxonium ions is expected to prompt a chain of oxidation reactions, resulting in reducing the size of the clustered molecules. The structure and stability of water cluster have recently been studied by computation and experiment. In computational chemistry, possible structures of ring-shaped clusters $(H_2O)_n$, n=3-60 are investigated. The computational results indicate that the bigger the ring is, the smaller the oxygen-to-oxygen distance is.

This may be because when the hydrogen bonding allows molecules to accept hydrogen, the hydrogen donating ability is enhanced due to a change in charge distribution. Hence, the bigger the water assembly, the stronger the hydrogen bonding cooperatively. This means that the smaller the size of clusters, the lower the heat of vaporization. Several isomers are predicted for hexamers of water molecules, and calculations show that ring, book, bag, cage and prism isomers share the nearly identical stability. For heptamers, two types of cage isomers are obtained by calculation. For octamers, cyclic and cubic forms are calculated. Other calculations predict monster clusters having a local minimum energy, such as fullerene-like 28-mer cluster, called "bucky water," and 280-water-molecule monster icosahedral network. In recent years, ab initio investigations have been carried out for analyzing water clusters.

Here, let us denote an evaporation rate and a heat of vaporization of water by v and Lv, respectively. The relationship between the evaporation rate v and the heat of vaporization Lv is given by the following Clapeyron-Clausius equation.

$$v = v_O \cdot \exp(-L_V/k_B T) \tag{1}$$

where $v_O$ is the constant of integration, $k_B$ is the Boltzmann constant, and T is the temperature.

Figure 4:
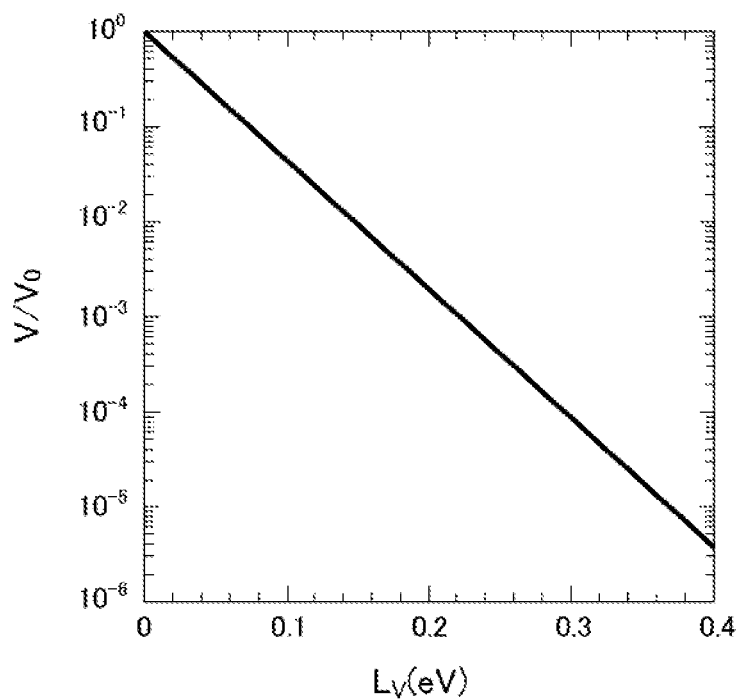
FIG. 4 is a graph used in illustrating a relationship between an evaporation rate v and a heat of vaporization Lv.

FIG. 4 is a graph illustrating a value of $v/v_O$ as a function of the heat of vaporization Lv. As can be seen from FIG. 4, the evaporation rate v increases with decrease in the heat of vaporization Lv. Therefore, the irradiation with oxonium ions prompts a chain of oxidation reactions, which causes reduction in size of the clustered molecules and decrease in the heat of vaporization, resulting in increase in the evaporation rate. Hence, it can be expected that when organic matter is irradiated with oxonium ions, much more water will be evaporated with the same energy. A verification test for drying capacity using oxonium ions will be described later in "Examples."

<Actions and Effects>

With the above-described configuration of the ion generating device 4 for organic matter decomposition, the needle electrode 12 and the plate electrode 13 face each other, and the direct-current power supply unit 9 is configured to apply the DC voltage with positive polarity to the needle electrode 12. The direct-current power supply unit 9 is configured to cause the voltage controller 10 to set the DC voltage to a specified voltage value, which produces positive corona discharge between the needle electrode 12 and the plate electrode 13 under atmospheric pressure.

According to the positive corona discharge produced between the needle electrode 12 and the plate electrode 13 of the ion generating device 4 for organic matter decomposition, it is possible to generate oxonium ions with high decomposition capability of organic matter. The ion generating device 4 for organic matter decomposition is configured to use the oxonium ions for organic matter decomposition, which makes it possible to enhance the decomposition capability of organic matter more than ever before.

In the ion generating device 4 for organic matter decomposition, the needle electrode 12 and the plate electrode 13 face each other to produce positive corona discharge in the hollow space ER1 of the electrode supporting member 14. With this configuration, the ion generating device 4 for organic matter decomposition is able to emit the oxonium ions only through the opening end of the tubular electrode supporting member 14. Since the direction of the opening end is thus selected, the oxonium ions can be emitted intensively only in the intended direction. Hence, the ion generating device 4 for organic matter decomposition is able to prevent the oxonium ions from scattering radially within the housing 8, and to transfer the oxonium ions further in the intended direction.

Moreover, in the ion generating device 4 for organic matter decomposition, the electrode supporting member 14 is placed such that the outlet of the housing 8 is located on the central axis X of the hollow space ER1, allowing the gas, which has been introduced into the housing 8 through the inlet from the blower 3, to linearly flow toward the outlet via the hollow space ER1. With this configuration, the ion generating device 4 for organic matter decomposition is able to introduce the oxonium ions generated in the hollow space ER1 directly into the tank 2 through the outlet. Since a region where the oxonium ions are sprayed within the housing 8 is thus limited, it is possible to prevent the housing 8 from being damaged by the oxonium ions with strong oxidation power.

Other Embodiments

The present invention is not limited to the above embodiment, and equivalent alterations and modifications to the above environment are possible within the scope of the present invention. For example, the electrode structure 11 may be placed at various locations within the housing 8. In the above embodiment, the organic matter decomposition device 1 is configured to heat and stir organic matter while irradiating the organic matter with oxonium ions to decompose the organic matter. However, the present invention is not limited to this embodiment. For example, the organic matter decomposition device may be configured only to irradiate organic matter with oxonium ions. Alternatively, the organic matter decomposition device may be configured to either heat or stir organic matter while irradiating the organic matter with oxonium ions.

Examples

Next, as with the typical example using the electrode structure 11 describe above, positive corona discharge is produced under atmospheric pressure when the DC voltage with positive polarity of 20 kV is applied to the needle electrode 12, and the plate electrode 13 is grounded. A verification test for measuring a number density of the generated oxonium ions is conducted. In this test, the number density of oxonium ions at each distance x from the electrode structure 11 where the oxonium ions are generated is measured using an ion counter (Brand name: Ion Counter NKMH-103 (ultra-wide range) manufactured by Ion Trading, Universal Plan Co., Ltd.). The results of the measurement are obtained as shown in FIG. 5.

Figure 5:
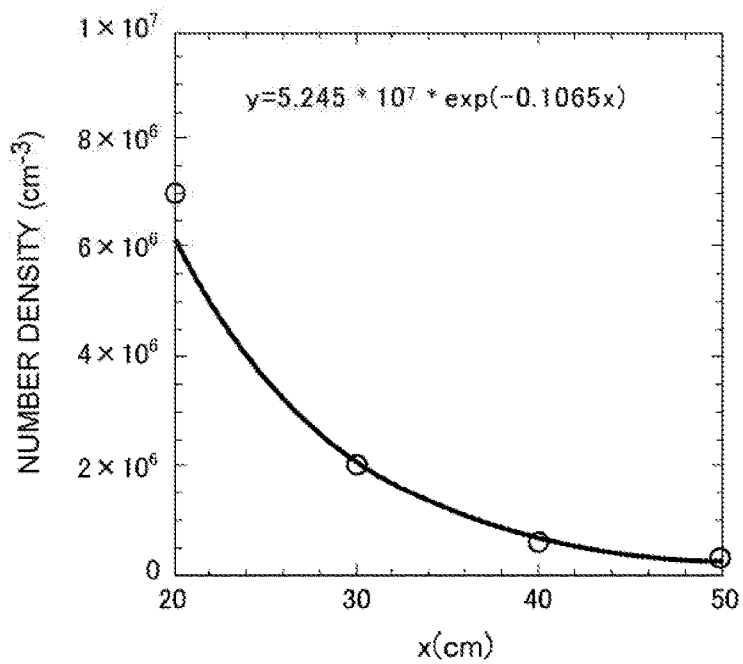
FIG. 5 is a graph illustrating a number density of oxonium ions at a distance x from a location where the oxonium ions are generated.

In FIG. 5, the measured values by the ion counter are denoted by circle, and an exponential function fitted to the measured values is denoted by a solid line. In the vicinity of the distance x=0 cm, fifty million oxonium ions or more per cubic centimeter ($cm^3$) are believed to be generated. As shown in FIG. 5, the number density of oxonium ions gradually decreases with increase in the distance x. It is therefore desirable the electrode structure 11 should be placed close to organic matter to be decomposed so that the oxonium ions can reach the organic matter directly.

Next, the verification test for evaluating the drying capacity of oxonium ions is conducted. In this test, four polymer absorbers which have absorbed sufficient amount of water (hereinafter referred to as aqueous polymer absorbers) are prepared. The four aqueous polymer absorbers, each of which weighs 100 g, are put into four containers (Tupperware®), respectively. As with the typical example using the electrode structure 11 describe above, the DC voltage of 20 kV is applied to the needle electrode 12 to produce positive corona discharge and thus generate oxonium ions. A first one of the four aqueous polymer absorbers is irradiated with the generated oxonium ions.

A second one of the four aqueous polymer absorbers is irradiated with negative ions and ozone, using an ionizer and an ozonizer (Ionizer MHM305 manufactured by Murata Manufacturing Co., Ltd., and Ionizer/Ozonizer MHM306 manufactured by Murata Manufacturing Co., Ltd.) as a comparative example 1. The condition for the irradiation is to continuously irradiate the second one of the four aqueous polymer absorbers with negative ions and ozone for about 48 hours. The voltage of 2 kV is applied per product specifications.

A third one of the four aqueous polymer absorbers is irradiated with negative ions only, using an ionizer (Ionizer MHM305 manufactured by Murata Manufacturing Co., Ltd., and Ionizer/Ozonizer MHM306 manufactured by Murata Manufacturing Co., Ltd.) as a comparative example 2. The condition for the irradiation is to apply the voltage of 2 kV per product specifications.

A fourth one of the four aqueous polymer absorbers is dried naturally without being irradiated with oxonium ions, negative ions, ozone or other particles.

Figure 6:
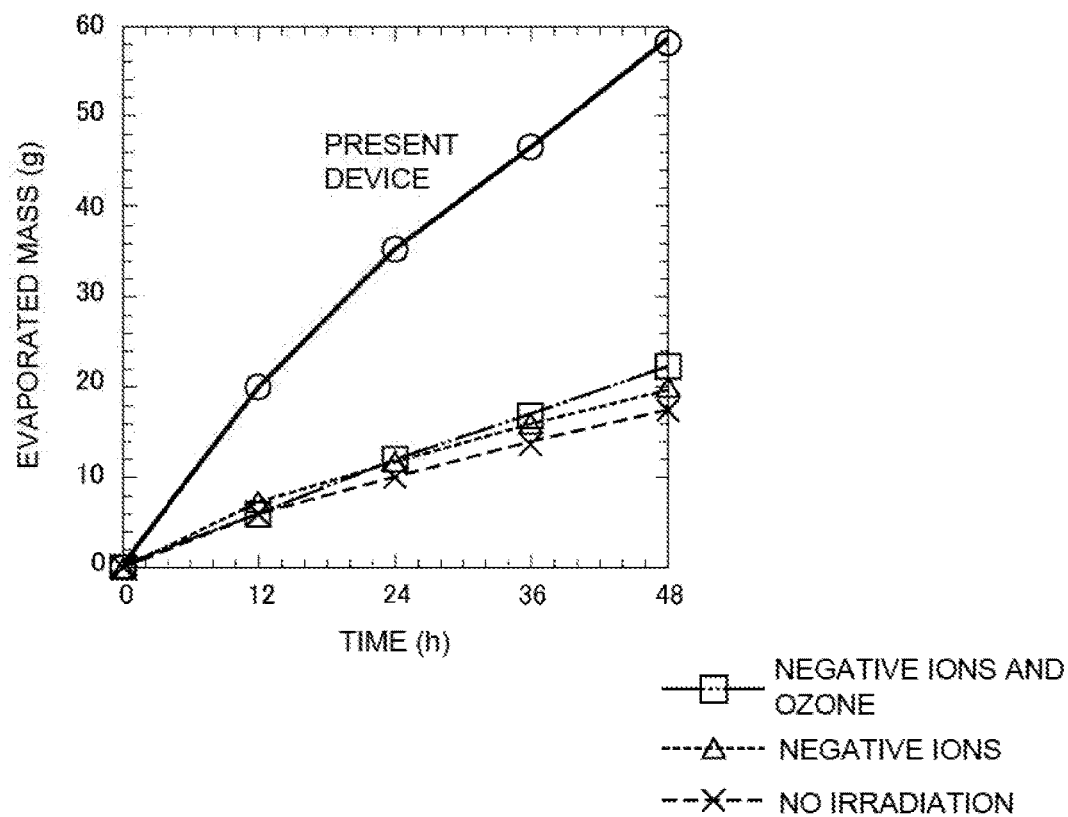
FIG. 6 is a graph illustrating results of measuring evaporated mass of aqueous polymer absorbers when irradiated with oxonium ions, when irradiated with negative ions and ozone, when irradiated with negative ions only, and when not irradiated with ions or other particles.
Figure 7:
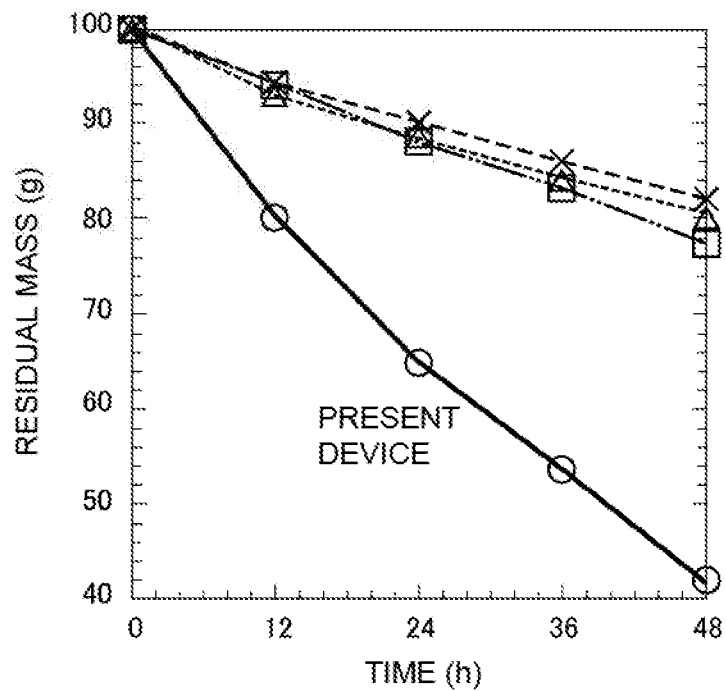
FIG. 7 is a graph illustrating results of measuring residual mass of aqueous polymer absorbers when irradiated with oxonium ions, when irradiated with negative ions and ozone, when irradiated with negative ions only, and when not irradiated with ions or other particles.

Under these conditions, evaporated mass and residual mass of the four aqueous polymer absorbers are measured every 12 hours for 48-hour period. The measurement results are obtained as shown in FIGS. 6 and 7. In FIGS. 6 and 7, the measurement results of the Example are indicated with "Present Device" and denoted by circle, and the measurement results of the comparative example 1, the comparative example 2, and no irradiation case are denoted by square, triangle, and cross mark, respectively.

The residual mass is measured with KD-192 manufactured by TANITA corporation. The evaporated mass is obtained by subtracting the residual mass form initial mass. As can be seen from FIGS. 6 and 7, regarding the comparative example 1 of the irradiation with negative ions and ozone and the comparative example 2 of the irradiation with negative ions only, each of the evaporated mass and the residual mass is almost the same as that of the no irradiation case.

In contrast, as for the Example of the irradiation with oxonium ions, it is found that the evaporated mass is exceptionally large, and the residual mass is exceptionally small, compared to those of the comparative example 1, the comparative example 2 and the no irradiation case.

Next, an aqueous polymer absorber which is the same as the one used in the verification test described above is prepared, and the electrode structure 11 of the Example is placed separately from the aqueous polymer absorber by 50 cm. After that, the aqueous polymer absorber is irradiated with oxonium ions. Evaporated mass and residual mass of the aqueous polymer absorber are measured every 12 hours for 48-hour period. The measurement results are obtained as shown in FIGS. 8 and 9.

Figure 8:
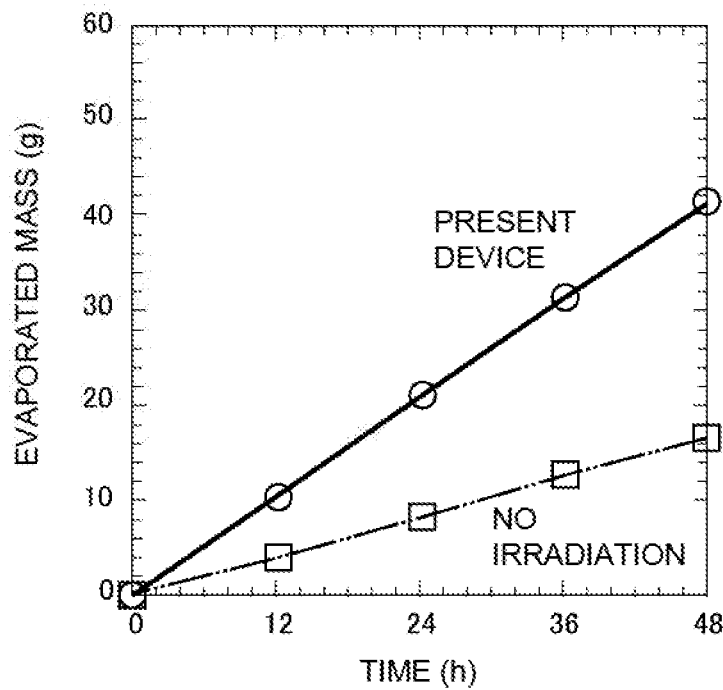
FIG. 8 is a graph illustrating results of measuring evaporated mass of aqueous polymer absorbers when irradiated with oxonium ions from a location separated from the aqueous polymer absorber by 50 cm, and when not irradiated with ions or other particles.
Figure 9:
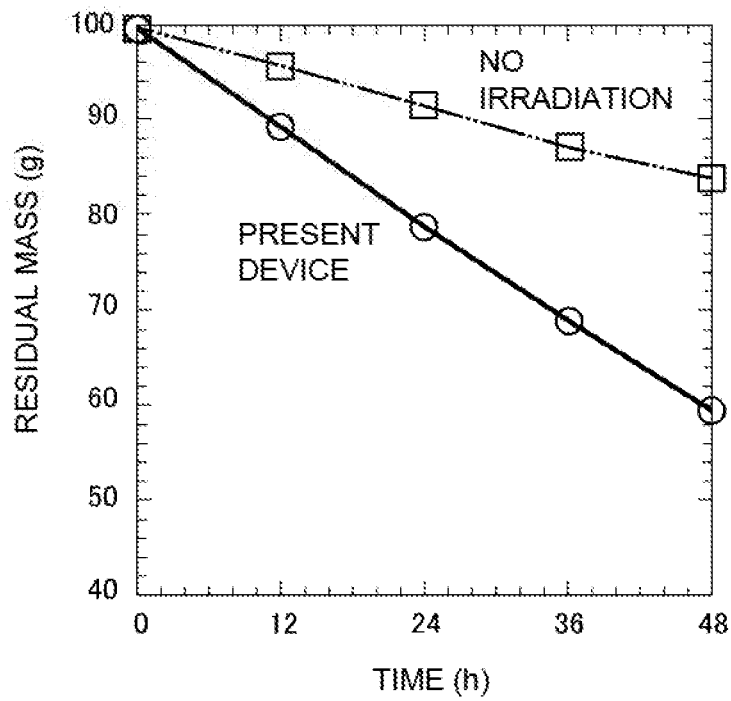
FIG. 9 is a graph illustrating results of measuring residual mass of aqueous polymer absorbers when irradiated with oxonium ions from a location separated from the aqueous polymer absorber by 50 cm, and when not irradiated with ions or other particles.

In FIGS. 8 and 9, measurement results of no irradiation case are also shown as a comparative example. As can be seen from FIGS. 8 and 9, the evaporated mass is quite large, and the residual mass is quite small even when the electrode structure 11 is separated from the aqueous polymer absorber by 50 cm. Hence, it can be said that sufficient amount of evaporation of water is ensured even when the electrode structure 11 is separated from the aqueous polymer absorber by 50 cm.

Figure 10:
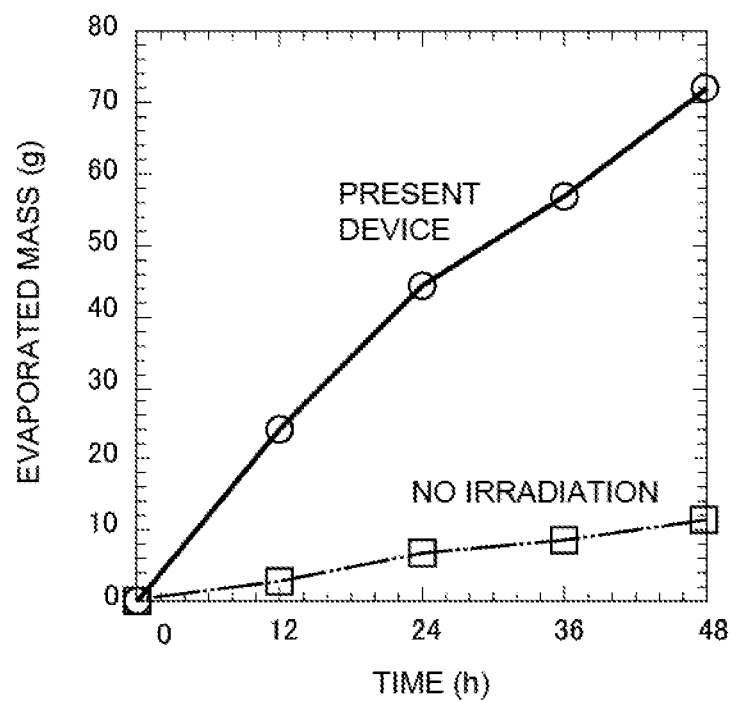
FIG. 10 is a graph illustrating results of measuring evaporated mass of water when irradiated with oxonium ions, and when not irradiated with ions or other particles.
Figure 11:
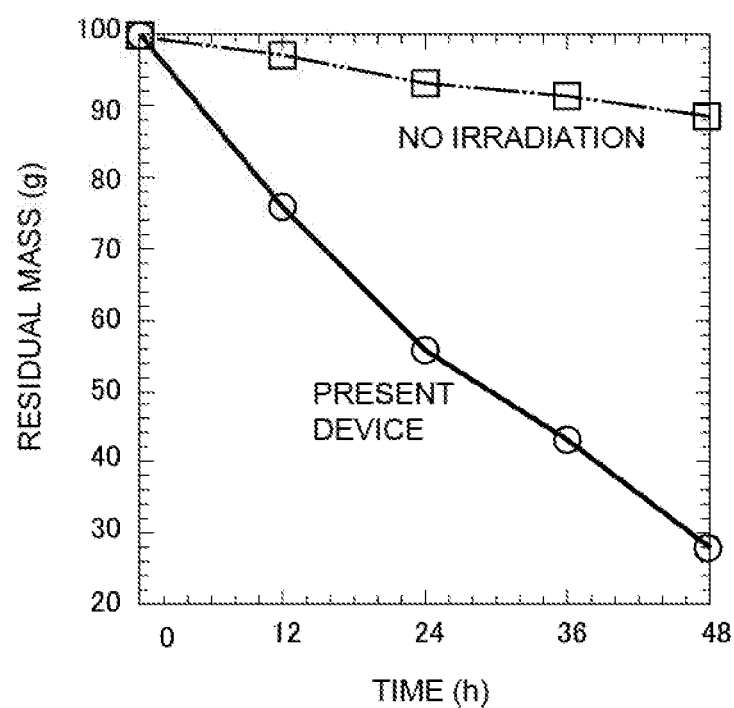
FIG. 11 is a graph illustrating results of measuring residual mass of water when irradiated with oxonium ions, and when not irradiated with ions or other particles.

Next, two containers (Tupperware®) are prepared, and 100 cc of water are put into each container. The electrode structure 11 is placed above and obliquely to a first one of the two containers so as to be separated from each other by 5 cm. After that, the water in the first one of the two containers is irradiated with oxonium ions generated by the electrode structure 11. The water in a second one of the two containers remains untouched. Under these conditions, evaporated mass and residual mass of water are measured every 12 hours for 48-hour period. The measurement results are obtained as shown in FIGS. 10 and 11.

In the Example of the irradiation with oxonium ions, it is found that the evaporated mass is exceptionally large, and the residual mass is exceptionally small, compared to those of the untouched water (indicated with "No Irradiation" in the drawings).

As described above, the Examples in which the needle electrode 12 and the plate electrode 13 are supported by the tubular electrode supporting member 14 and the high DC voltage of 20 kV is applied to the needle electrode 12, are found to be largely effective in evaporation of water even at places separated by 5 cm or 50 cm. By employing the configuration of the Examples, we assume that the oxonium ions generated by the electrode structure 11 fly further with a higher velocity.

In the above embodiment, the gas from the blower 3 is introduced into the housing 8 through the inlet. However, the present invention is not limited to this embodiment. For example, an exhaust device like a blower may be provided on an external exhaust opening of the tank 2. The exhaust device may be configured to exhaust the gas from the tank 2 to the outside to draw gas from the housing 8 into the tank 2, thereby introducing gas (air) into the housing 8 through the inlet. This configuration also makes it possible to introduce the gas into the housing 8 through the inlet and transfer the gas into the tank 2 through the outlet.

REFERENCE SIGNS LIST 1 organic matter decomposition device
2 tank
3 blower
4 ion generating device for organic matter decomposition
8 housing
9 direct-current power supply unit
10 voltage controller
12 needle electrode
13 plate electrode
14 electrode supporting member

The invention claimed is:

1. An ion generating device for organic matter decomposition for generating ions to decompose organic matter stored in a tank, the ion generating device comprising:
a needle electrode and a plate electrode, both facing each other; and
a direct-current power supply unit configured to apply a direct-current voltage with positive polarity to the needle electrode, the direct-current power supply unit including a voltage controller configured to set the direct-current voltage having a value of 5 kV to 30 kV and an electrical field strength of 0.25 kV/mm to 1.5 kV/mm to produce positive corona discharge between the needle electrode and the plate electrode under atmospheric pressure, thereby generating oxonium ions.

2. The ion generating device for organic matter decomposition according to claim 1, further comprising a tubular electrode supporting member for supporting the needle electrode and the plate electrode,
the tubular electrode supporting member having a tubular inner wall surrounding a hollow space in which the needle electrode and the plate electrode face each other to produce the positive corona discharge within the hollow space.

3. The ion generating device for organic matter decomposition according to claim 2, further comprising a housing within which the tubular electrode supporting member is placed, the housing including an inlet through which gas is configured to be introduced, and an outlet through which the gas is configured to flow into the tank, wherein
the tubular electrode supporting member is placed such that the outlet is located on a central axis of the hollow space, and
in the housing, the gas introduced through the inlet is configured to linearly flow toward the outlet via the hollow space.

4. An organic matter decomposition device, comprising:
the ion generating device for organic matter decomposition according to claim 1; and
the tank on which the ion generating device for organic matter decomposition is provided.

5. An organic matter decomposition device, comprising:
the ion generating device for organic matter decomposition according to claim 2; and
the tank on which the ion generating device for organic matter decomposition is provided.

6. An organic matter decomposition device, comprising:
the ion generating device for organic matter decomposition according to claim 3; and
the tank on which the ion generating device for organic matter decomposition is provided.

* * * * *